(12) United States Patent
Saleh (10) Patent No.: US 8,142,443 B2
(45) Date of Patent: Mar. 27, 2012

(54) SURGICAL RETRIEVAL DEVICE RADIALLY DEPLOYABLE FROM A COLLAPSED POSITION TO A SNARE OR CAUTERIZATION LOOP

(76) Inventor: Rafic Saleh, Aguadilla, PR (US)

( * ) Notice: Subject to any disclaimer, the term of this patent is extended or adjusted under 35 U.S.C. 154(b) by 552 days.

(21) Appl. No.: 12/215,298

(22) Filed: Jun. 25, 2008

(65) Prior Publication Data

US 2009/0024139 A1  Jan. 22, 2009

Related U.S. Application Data

(63) Continuation-in-part of application No. 12/074,885, filed on Mar. 7, 2008.

(60) Provisional application No. 60/961,187, filed on Jul. 18, 2007.

(51) Int. Cl.
*A61B 17/24* (2006.01)
*A61B 17/22* (2006.01)

(52) U.S. Cl. ........................................ 606/113; 606/128

(58) Field of Classification Search .................. 606/127, 606/128, 110, 113, 114, 115, 123, 45, 32, 606/112, 200; 600/562, 564
See application file for complete search history.

(56) References Cited

U.S. PATENT DOCUMENTS

| 6,585,734 B2 * | 7/2003 | Levinson .......................... 606/47 |
| 2003/0176888 A1 * | 9/2003 | O'Connell .................... 606/200 |
| 2005/0119668 A1 * | 6/2005 | Teague et al. .................. 606/127 |

* cited by examiner

*Primary Examiner* — Kathleen Sonnett
*Assistant Examiner* — Jocelin Tanner
(74) *Attorney, Agent, or Firm* — Donn K. Harms (57) ABSTRACT

A surgical instrument featuring a combination cauterizing and surgical capture component. The instrument is deployable from a distal end of a lumen to a first position partially exposing a cauterizing loop and restrained radially deployable members wherein a plurality of cauterizations may be performed. The instrument is deployable to a second position fully translated from the lumen wherein the plurality of radially positionable members may be released by activation of a release member to allow the biased members to deploy radially around an axis running through the loop.

8 Claims, 8 Drawing Sheets

SURGICAL RETRIEVAL DEVICE RADIALLY DEPLOYABLE FROM A COLLAPSED POSITION TO A SNARE OR CAUTERIZATION LOOP

This application is a Continuation in Part of U.S. patent application Ser. No. 12/074,885 filed on Mar. 7, 2008 which claims the benefit of U.S. Provisional Application No. 60/961,187 filed on Jul. 18, 2007 both of which are incorporated herein in their entirety by reference.

FIELD OF THE INVENTION

The disclosed device relates to retrieval devices for use in surgery. More particularly the disclosed device relates to a design and assembly for an expandable surgical instrument for employment within internal body cavities. The device features a capture basket that is deployable in a retracted position and which will double as a cauterization tool while in the retracted position. The device being biased to expand while concurrently held in the retracted position will, upon release of the means of restraint of the plurality of biased members, form a capture component.

BACKGROUND OF THE INVENTION

Laparoscopic or similar surgeries where a tube with a light and a camera lens at the end (laparoscope) is employed to examine organs, check for abnormalities, or perform minimally invasive surgeries are a desirable alternative to prior surgical techniques requiring large incisions. In a similar fashion, procedures in gastroenterology employ such devices to search for and remove colorectal polyps which form on the lining of the intestine.

Such procedures generally employ a small camera adjacent to the instruments inserted through small incisions in the patient's body, or into cavities of the patient's body. Such procedures may involve removal of tissue for a specific ailment, such as the gall bladder, or may be exploratory in nature where tissue samples are taken and removed from the body for examination and testing. Just a few such operations include but are not limited to, a polypectomy, a bronchoscopy, a bulboscopy, a colonoscopy, a duodenoscopy, an endoscopy and a gastroscopy. Rather than a catheter type device, when used for low invasive procedures through the lower intestine such devices are also specialized as for Endoscopy or in many other specialized versions including but not limited to a gastroscope, or colonoscope, or sigmoidiscope or bronchoscope. These types of devices generally have the video component following a collinear path in a common flexible conduit.

Manually operable surgical devices employed for such procedures inside a patient's body by a surgeon from a position outside the patient are widespread and well known. In a conventional procedure, the cutting and retrieval components employed by the surgeon are located at the distal end of the surgical instrument. In a conventional polyp removal procedure, an endoscope is inserted into an internal cavity of a patient, and manipulated to search for any abnormal tissue growths such as polyps. If tissue such as a polyp is located for removal, a wire extending through an elongated pathway in the biopsy channel of the endoscope is translated toward the distal end of the device to project a cauterization loop connected to the wire from the distal end of the pathway running through the endoscope. Using a video display, the surgeon then manipulates the loop and the endoscope from outside of the patient and engages the loop with the polyp. The wire is positioned around the base of the polyp whereafter an electrical current is communicated to the loop to cut and cauterize the region.

As can be ascertained, in such a procedure, where tissue is removed for sampling or as an object of the procedure, it is imperative that the surgeon is able to view the tissue in question at the distal end of the surgical device deployed into the patient. Viewing is conventionally achieved over a fiberoptic link from a lens to a video display viewed by the surgeons outside the body of the patient.

Avoiding interference with the view of the surgeon, is particularly important when small tissue samples are being removed such as a polypectomy because the polyps being removed are small and easily missed. Further, once removed, they must be located and retrieved with a retrieval component.

Unfortunately, conventional capturing devices for this purpose, are formed as nets or netting in a fine mesh. The mesh, especially in the small confines of body cavities such as the intestine, can severely impair the view by blocking it from camera view. Further, the interconnecting mesh of such devices communicates electrically or offers the potential for such, and they are inhibited from functioning as both the snare or tissue removal instrument as well as the catch basket in combination. Other wire formed baskets employed for the purpose impart the same visual impairments as mesh type capture devices.

As such, using conventional mesh net style retrieval components, or wire-formed capture components, subsequent to locating and removing a polyp or other tissue portion by the electrified cauterization component, is a difficult task due to the impairment of the view of the internal cavity. Additionally, most such net style or wire formed retrieving components, are not easily positionable around the tissue, or around a lost surgical device, because the netting which is engaged around the mouth of the net, impairs or prevents positioning and rotation of the mouth in the small confines of an intestine or other small body cavity.

The device and method herein disclosed and described features a cutting or cauterizing component to which a radially deployable capturing component is initially engaged in a retracted position. The capturing component is formed of radially oriented members extending from mouth portion which forms the cutting or cauterizing component. The shape of the members is infinite as is the number and positioning thereof. The members can thus collapse to form virtually any shape planar component such as an oval, a crescent, a hexagon, or any other geometric shape to which the radially deployable members or members can be formed.

The radial deployment is also infinitely variable in both the number of deployable members or wires, and their deployment around the axis formed by the distal end of the wire engaging them. Thus the capture component can be deployed radially around the axis from a full 360 degrees down to a minimum required to form a capture component such as 100 degrees or more preferably 180 degrees of radial deployment.

Unlike most netting or mesh basket collection components, or other wire or member-formed capture components, the radially oriented wires forming the capture component or catch basket of the device herein disclosed, in the retracted position, are rotated from their relative positions around the axis to adjacent positions abutting each other. This forms a generally planar snare or elongated member which operates as the cauterizing or cutting component while the device is retracted.

Of course the device can also be employed simply as a deployable capture component without the cauterizing or cutting loop and still be a great improvement to the art. With the plurality of wires or elongated members forming loops in virtually any geometric shape, the device, as a capture component, can be deployed in the collapsed position with the radially deployable loops restrained adjacent to each other to form a generally planar loop member. Once properly positioned, the means for restraint can be released wherein the loops will deploy radially around the axis extending from the control wire they engage. As noted the formed capture component can be of any shape to which the members forming the loops are shaped and can be in any number and at any radial deployment as suits the purpose all the way to a 360 degree deployment of spaced members.

When employed with a cauterizing or cutting members, during the initial cutting procedure, the radially deployable members forming the basket, are compacted and engaged to a formed mouth portion, out of view of any video cameras. This retractable position markedly increases the field of view for the surgeon trying to cut or cauterize tissue.

Also noted, there is employed a restraint device to maintain the radially deployable members or wires forming the basket or capture component in the collapsed position. This restraint device may be a heat released restraint which will automatically deploy the members radially to form the capture component when the aperture heats to cut or cauterize. Or, the restraint device may be mechanical in nature where a force or a wire operated release component is employed to release the members from their constrained position out of view to expand radially around the axis to the degree desired. Other releasable means for restraint of the radially deployable members can be employed such as hook and loop fabric, tape, or any means for releasable restraint as would occur to those skilled in the art.

Consequently, a surgeon viewing the intended target using the camera with the radially deployable members constrained by the restraint device, has an uninterrupted view of the tissue to be removed or retrieved for a much improved view for the surgeon on the viewing screen outside the body of the patient. The surgeon can thus easily see even the smallest tissue to be retrieved and rotate or manipulate the mouth of the radially formed catch basket over it. Once finished, the members forming the capture component such as a basket are deployed from the loop forming the aperture or the mouth to which they are radially abutted by the restraint device during the cutting or cauterizing procedure.

The members forming the loops of the capture component will best be biased to deploy to the radially deployed position spaced from each other and at positions around the center axis to form the capture component. This can be done during initial forming using shaped memory material which will return to its original position around the center axis or other means for biasing the members to a radial deployment at any spaced angular deployment around the axis.

All embodiments of the device enjoy this additional utility provided by their radially oriented wire formation of the capture component or basket from this restrained position to the released position. As noted, an infinite number of geometric shapes may be employed for the radially deployable members or loops and when retracted, the shape of the mouth or aperture of the capture component is substantially similar to that of the deployable loop members.

In this respect, before explaining at least one embodiment of the invention in detail, it is to be understood that the invention is not limited in its application to the details of construction and to the arrangement of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the pioneering conception of a radially expandable biased capture component upon which this disclosure is based, may readily be utilized as a basis for designing other methods and systems for carrying out the several purposes of the present invention of a tissue retrieval system for surgery. It is important, therefore, that the claims be regarded as including such equivalent construction insofar as they do not depart from the spirit and scope of the present invention.

An object of this invention is the provision of a cutting and cauterizing loop to which an underlying basket or capture component is retractable and held by a heated or mechanically releasable restraint, thereby enhancing the view of the tissue during the cutting or cauterizing procedure.

An additional object of this invention is the provision of such a retrieval or capture component which is formed from radially deployable members having gaps therebetween which is deployable from a retracted substantially planar position by releasing a restraint which may be heat released, mechanically released, or otherwise released.

Another object of this invention is the formation of a radially deployable capture component formed in virtually any geometric shape which may be employed singularly or in combination with a cauterization loop.

An additional object of this invention is the formation of a capture component by deployment of biased radially deployable members to spaced positions anywhere around an axis.

These together with other objects and advantages which will become subsequently apparent reside in the details of the construction and operation as more fully hereinafter described and claimed, reference being had to the accompanying drawings forming a part thereof, wherein like numerals refer to like parts throughout.

SUMMARY OF THE INVENTION

The tissue or foreign body capturing component herein described and disclosed may be employed as a capture component or in combination with a cauterization snare component which is integral to the radially deployable capture component or catch basket. When deployed as a combination component, the mouth edge of the catch basket is formed by a cauterization snare which would be formed of a non-insulated conductor which may be energized to heat for cutting and cauterization. When deployed solely as a capture component, the mouth edge would be formed of a centrally located pair of radially deployable members.

The members forming the device may be formed in virtually any geometric shape for instance an oval, a hexagon, or any other shape. The number, spacing, and radial deployment of the members forming the capture component are also infinitely variable. Consequently any number of members may be deployed to expand to any angular radial deployment around a center axis once released from a collapsed position engaged to the centrally positioned pair of members forming the mouth. This angular deployment can be 360 degrees or less and spacing appropriate to leave voids between the members to capture the targeted item or tissue.

The members forming the capture component or basket are formed and biased using memory shape material or other means to radially bias to thereby deploy once released from a collapsed position by a means for restraint. The restraint may be one that will melt at a defined temperature and release the basket to radially deploy, or may be a mechanical release or any releasable means for restraint as would occur to those skilled in the art.

The mouth portion and the members forming the capture component are both collapsible to thereby allow for a translatable engagement through an axial passage for a deployment such as a catheter or colonoscope, or similar type device having a control wire or lumen engaged at a first end of the device which runs axially to a surgeon-manipulable actuator at a second end for controlling the wire at the first end. The capturing component has a catch basket which is translatable from within the distal end of the tube or conduit housing it, and, once so deployed, if not used to capture tissue, it may be translated back into the tube from which it was deployed.

This easy translation and forming of both the mouth portion which may be a cauterization loop and the engaged and restrained biased members deployable to form the capture component, along with other utility herein described, is provided by forming the catch basket from a plurality of radially oriented and spaced members extending radially from the mouth or cauterization loop. The catch basket extends radially around a central axis extending forward from the lumen engaging it to any angular displacement around the axis.

The advantage of collapsing the basket against the mouth or cauterization loop with the appropriate releasable restraint is an extremely enhanced view of the tissue. The capture component may be automatically deployed by a heat sensitive restraint, or may be mechanically released using a control mechanism to release a knot, break a seal or tape, or otherwise release the deployable members from the mouth portion.

The device, once extended from the distal end of the tube or conduit carrying it, initially can deploy the snare or cauterization loop forming a mouth portion of the capture component that is collapsed against it by the restraint device. The snare or cauterization loop is formed of two side members extending in the same plane to yield the desired dimensioned opening for the collapsed basket once deployed thereunder. If a cauterization loop is combined with the capture component, the members forming the cauterization loop would be non-insulated to allow for reaction with body tissue once energized. The members forming the capture component would best be insulated or non conducting so as not to react with body tissue.

The unique radial formation of the snare or cauterization loop forming the mouth, and the radially deployable biased members secured thereto, will allow for re-collapse of both the mouth portions, and the radial wire portions, and consequently easy translation back into the catheter. If employed to capture tissue or anything else, translation of the device back into the catheter also causes the mouth portion to close and create an ever shrinking closed capture basket. The device will thus shrink in size to hold and retrieve even the smallest piece of tissue.

The device also allows deployment and capture of tissue or foreign objects using a controllable release and subsequent deployment of the members around the axis to enable a capture of an object. In such a method, the mouth portion formed by two members would be deployed to surround the object intended for capture. Then, the means for restraint of the radially deployable members would be released allowing the members to radially deploy around the axis and concurrently capture the object intended. The control wire engaging the mouth and deployable members would be retracted to close the mouth and thereby hold the captured object for retrieval. Activation of a release of the restraint can be by a mechanical release to cut a thread, untie a knot, release some type of restraint, or could be heat activated wherein a restraint is melted and the radially deployable members would move to the biased position around the axis.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. Therefore, the foregoing description and following detailed description are considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

DETAILED DESCRIPTION OF THE INVENTION

Figures 1, 2:
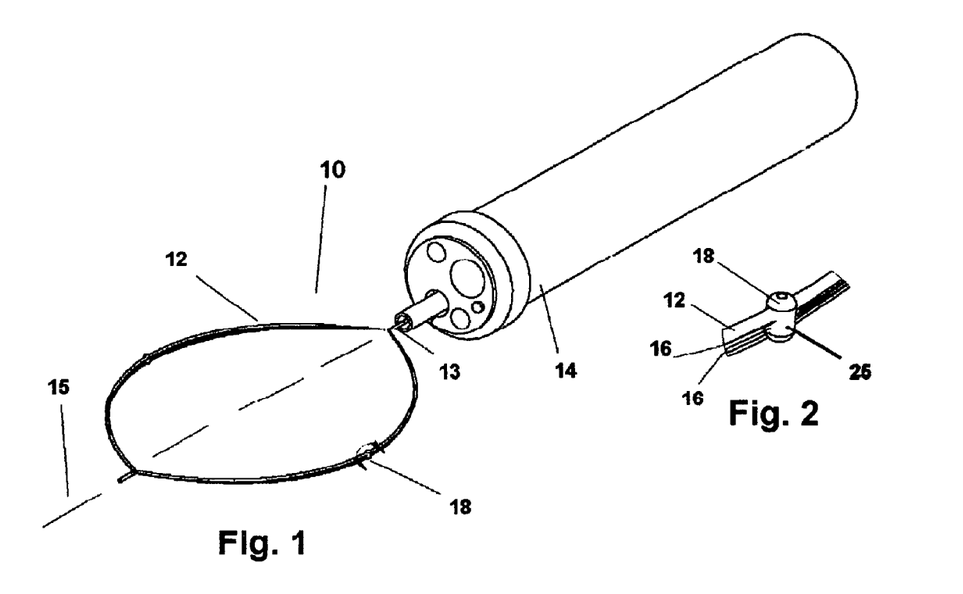
FIG. 1 shows a perspective view of the device employing a snare or cauterization loop deployed from a catheter in combination with the radially deployable members which form the capture component collapsed against it by a medical glue based restraint device.
FIG. 2 depicts the restraint device and the stacking of the underlying radially deployable members which will form the capture component or basket once the restraint is released.
Figure 12:
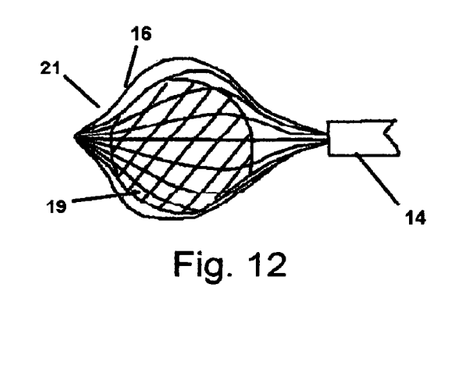
FIG. 12 depicts the capture component formed of the radially deployed biased members translated partially into the lumen such as a catheter or sheath and encircling a piece of material to be removed.

Referring now to the drawings in FIGS. 1-14, wherein similar parts are identified by like reference numerals, there is seen in FIG. 1 a perspective view of the device 10 in a generally crescent shape, wherein the snare or cauterization loop 12 formed of non-insulated conductive material, is deployed from a lumen such as a sheath or catheter 14 in a combination with the radially deployable members 16 which radially positionable around the axis 15 to form a collection or capture component 21 as in FIG. 12.

In all modes of the device 10 where a cauterization loop 12 is included, the loop 12 will be uninsulated and therefor reactive with tissue when electrified. Of course the device 10 can be employed with a loop 12 defining a mouth of the capture component 21 formed of insulated material just like the members 16 or of non electrifiable material if cauterization is not desired. Even in this mode without the cauterization, the biasing of the members 16 to move to an expanded position radially deployed provides great utility for a capture component 21 that is expandable at will to encircle material 19 such as tissue or a polyp for removal.

A control wire 13 is engaged to or communicates motion to the trailing ends of the loop 12 and members 16 to thereby translate and position the device 10 from the catheter 14. During deployment from the catheter 14 the members 16, which are formed of memory material or otherwise adapted to bias around the axis 15, are collapsed against or adjacent to the loop 12 by a means for restraint depicted restraint device 18. While depicted in FIG. 1 as a crescent shape, the loop 12 and capture component 21 formed by the members 16 of the device 10 may be formed in any geometric shape into which the loop 12 and members 16 can be formed. Also, in all modes of the device 10, while it may be shown as a 180 degree radial deployment around the axis 15 in a number of the drawings such as FIG. 3, the members 16 can be deployed in any radial deployment up to 360 degrees around the axis 15, and, can consist of a plurality of any number of members 16, and can be spaced at any distance from adjacently situated members 16 in such a radial deployment.

FIG. 2 depicts the restrain device 18 of FIG. 1 showing the means for restraint being a medical glue 25 which melts during heating of the cauterization loop 12. Such a means of restraint would result in an automatic deployment of the members 16 to form a capture component 21. The stacking of the underlying radially deployable members 16 is held by one or a plurality of the restraints 18 whereafter the members 16 which are biased outwardly, will radially deploy around the axis 15 from the loop 12 to which they were constrained.

Figure 3:
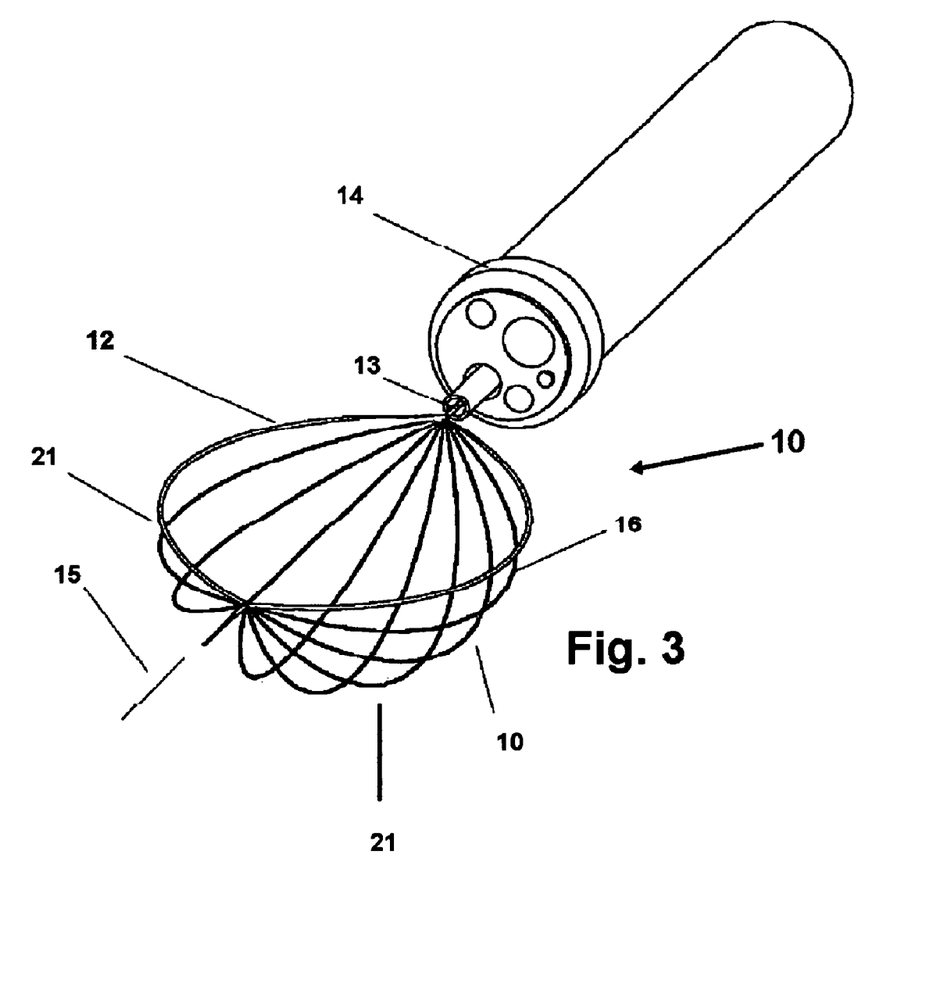
FIG. 3 depicts a crescent shaped mode of the device of FIG. 1, wherein the restraint has released from the heat of the cauterization loop and members have deployed to a basket shaped capture component and the mouth portion is formed by the conductive wires of the cauterization loop portion.

FIG. 3 depicts the device of FIG. 1, wherein the restraint 18 which as shown is medical glue, has completely released whereafter the members 16 have deployed to form a capture component 21 in the form of a basket. As noted, any number of members 16 at any spacing and any angular displacement around the axis 15 may be employed.

Figures 4, 5:
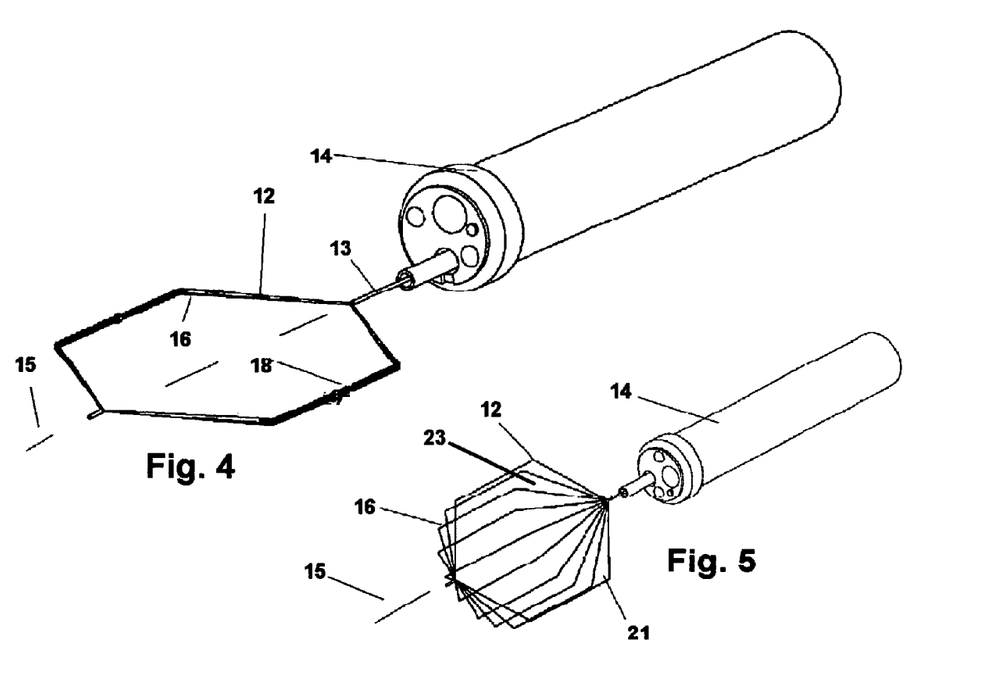
FIG. 4 shows the device in a different shape collapsed against the pair of members forming a mouth or cauterization loop in a six sided shape.
FIG. 5 depicts a perspective view of the device of FIG. 4 once the restraint is released.

FIG. 4 shows the device 10 in a different shape of six angular sides. As noted the members 16 forming the capture or collection component and the loop 12 can be any shape. When in the collapsed position as depicted, in FIG. 4 they will radially deploy around the axis 15 to form a similarly shaped capture component 21 for collecting tissue or foreign objects. The number, and the spacing, of the members 16 to form gaps 23 therebetween is infinitely variable in that any number of members 16 can be used in any spacing around the axis 15 thereby making the size of the gaps 23 infinitely variable.

FIG. 5 depicts a perspective view of the device of FIG. 4 once the restraint is released. As shown in a 180 degree spaced radial deployment, it is envisioned as noted that any spacing and any radial deployment of the members 16 around the axis 15 can be employed.

Figures 6, 6A:
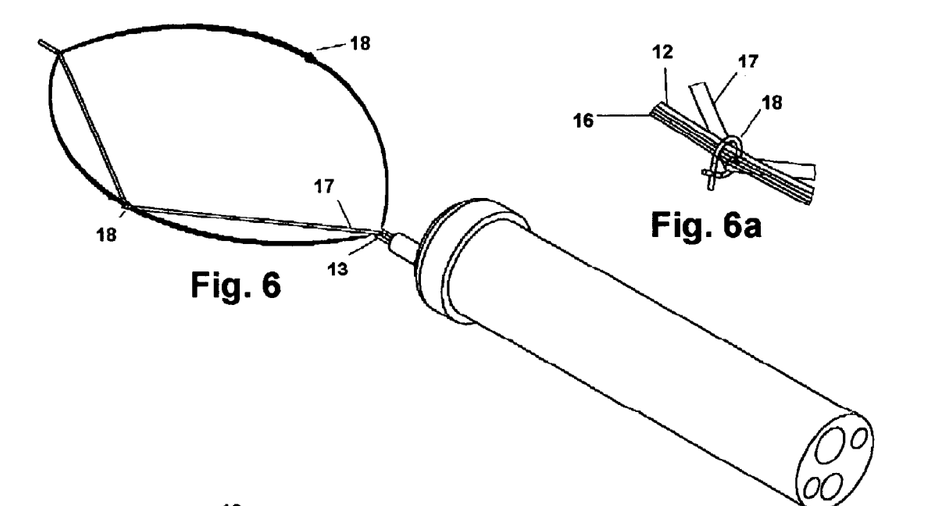
FIG. 6 depicts the device herein restrained by a knot.
FIG. 6a depicts a close up of the knot and release mechanism controlled by a release wire.

FIG. 6 depicts the device herein wherein the restraint 18 employed for means of restraint of the members 16 is a knot in an encircling loop of surgical thread, suture material or similar flexible material. One or a plurality of knots may be employed as needed. Translation of a release wire 17 separate from the control wire 13, provides means for controlled mechanical release of the means for restraint 18. FIG. 6a depicts a close up of the knot and release mechanism controlled by the release wire 17.

Figures 7, 7A, 8:
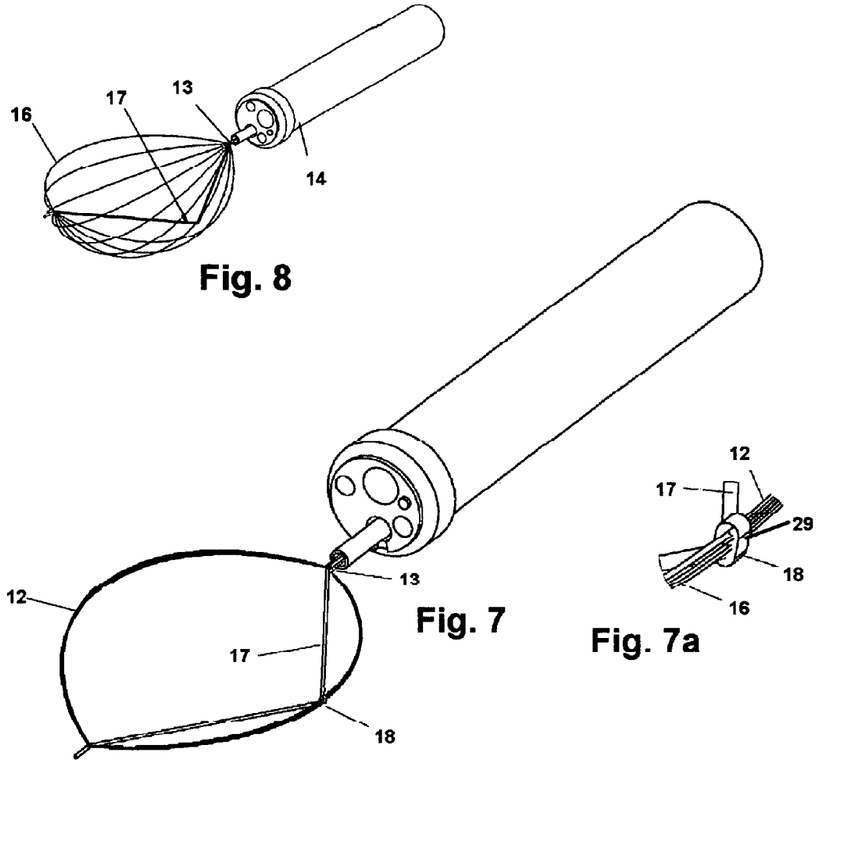
FIG. 7 depicts a mode of the device having the deployable members restrained by medical tape.
FIG. 7a depicts a close up view of the medical tape of FIG. 7 and the release mechanism control wire.
FIG. 8 depicts an embodiment of the device wherein the deployable members of the capture component expand radially around the axis to a 360 degree capture component.

FIG. 7 depicts a mode of the device having the deployable members 16 which are restrained by means of restraint in the form of medical tape 29 in one or a plurality of positions. A release wire 17 separate from the control wire 13, would provide a user operable mechanical means for controlled release of the release of the restraint 18 provided by the tape or other mechanically releasable means for restraining the members 16. FIG. 7a depicts a close up view of the medical tape of FIG. 7 and the release wire 17.

FIG. 8 depicts an embodiment of the device wherein the deployable members 16 of the capture component expand radially around the axis to a 360 degree mode of the capture component 21 with gaps 23 between the deployed members 16. As noted, any number of members 16 in any spacing scheme be it equal or unequal, in any radial deployment around an axis 15 may be employed depending on the intended task and all are considered included in this application. The 180 degree deployment depicted in FIG. 3 is a particular favorite having a defined mouth, however all modes of the device 10 allow for the capture component 21 to be pulled into the deploying lumen or catheter 14 as shown in FIG. 12, to a point where it will collapse around and hold, a captured piece of material 19 for removal, but other radial deployments may be more favorable depending on the procedure intended. When employed with a 360 degree deployment the gaps 23 would be manipulated over the material 19 to be removed and the capture component 21 retracted into the lumen as in FIG. 12 to tightly hold it.

Figures 9, 10:
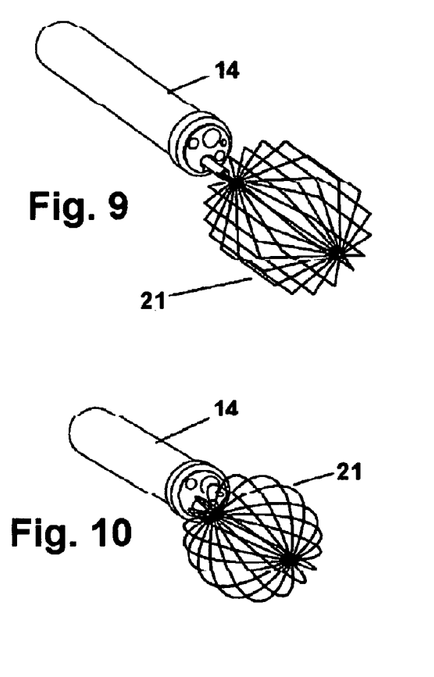
FIG. 9 depicts a substantially hexagonal shaped embodiment of the device deployed to a 360 degree capture component.
FIG. 10 depicts a substantially round shaped embodiment of the device deployed to a 360 degree capture component.

FIG. 9 depicts a mode of the device 10 having members 16 and a loop 12 formed to yield a substantially hexagonal shaped embodiment of the device 10 and also showing a deployment to a 360 degree capture component 21 with equidistant spacing and gaps 23. Any radial deployment around an axis may be employed and the plurality of members 16 and spacing thereof is infinitely variable depending on the desired spacing in the deployed position.

Figure 9A:
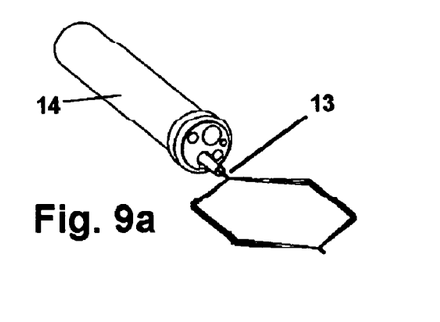
FIG. 9a depicts the device of FIG. 9 in a collapsed position substantially planar shape with the deployable members forming the plurality of loops engaged to a center loop which can double as a cauterization loop.

In FIG. 9a the device 10 in the hexagonal shape of FIG. 9 is shown in the collapsed position substantially planar shape. As with the other modes and shapes of the device 10, the members 16 are engaged to either the loop 12 or the control wire 13 in a fashion to cause a bias of the members 16 around an axis once the means for restraint to hold the members 16 in a collapsed position adjacent to the loop 12 is released. Also as noted this means for restraint on any mode may be glue, tape, a knot, or any means for restrain that may automatically release with heat, or relapse with a release wire 17, or any means for restraint that is adapted to the task and would occur to those skilled in the art.

Figure 10A:
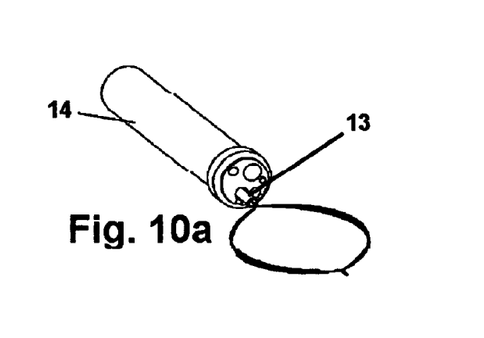
FIG. 10a depicts the device of FIG. 10 in a collapsed position substantially planar shape with the deployable members forming the plurality of loops engaged to a center loop which can double in the preferred mode as a cauterization loop.

As with FIG. 9, FIG. 10 depicts a 360 degree deployed capture component 21 formed of members 16 yielding a substantially round shaped embodiment of the device 10. FIG. 10a depicts the device of FIG. 10 shown in a collapsed position having a substantially planar round shape with the deployable members 16 restrained adjacent to the centered loop 12 which can double in the preferred mode as a cauterization loop and in that case would be uninsulated.

Figure 11:
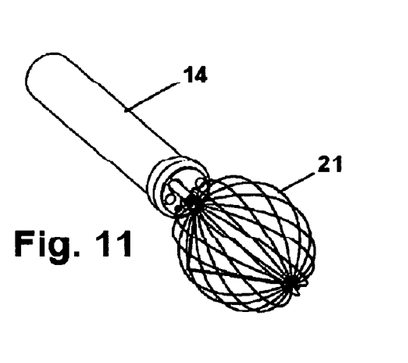
FIG. 11 depicts a substantially oval shaped embodiment of the device deployed to a 360 degree capture component 21.

In FIG. 11 there is shown a substantially oval shaped embodiment of the device 10 with the members 16 in a deployed position forming a capture component 21 which encircles 360 degrees around an axis. As with the other embodiments, the members 16 are shaped with memory material to retain the shape induced and the members 16 are biased to move to positions around a center axis when released. This bias can be provided by forming the members 16 using shape memory material such as nitinol while they are in a radially deployed position and then restraining them to a collapsed position thereby providing a memory material as the means for radially biasing the members 16. Or a spring engaged to the connection points of the members 16 to the control wire may be employed or other means to bias each member 16 to a radially located position around the axis as would occur to those skilled in the art.

Figure 11A:
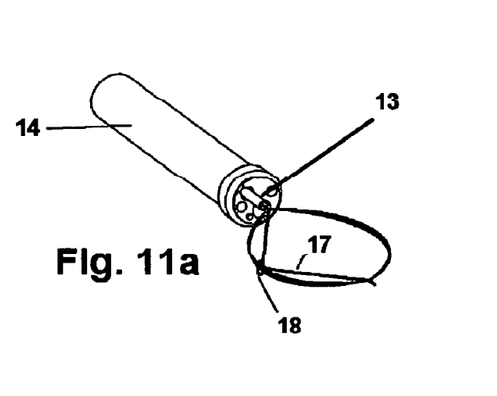
FIG. 11a depicts the device of FIG. 11 in a collapsed position substantially planar shape with the deployable members forming the plurality of loops engaged to a center loop which can double as a cauterization loop.

FIG. 11a depicts the device of FIG. 11 in a collapsed position substantially planar shape with the deployable members 16 forming the plurality or radially located portions of the capture component 21 when deployed, collapsed adjacent to a center loop 12 which can double as a cauterization loop. As in other modes, the members 16 are formed to bias against the restraint to the collapsed position and return to a specific position of radial deployment.

FIG. 12 depicts the capture component formed of the radially deployed biased members 16 which are translated partially into the lumen such as a catheter or sheath by translating the control wire thereby causing an encircling of a piece of tissue 19 or material to be removed.

Figures 13, 13A:
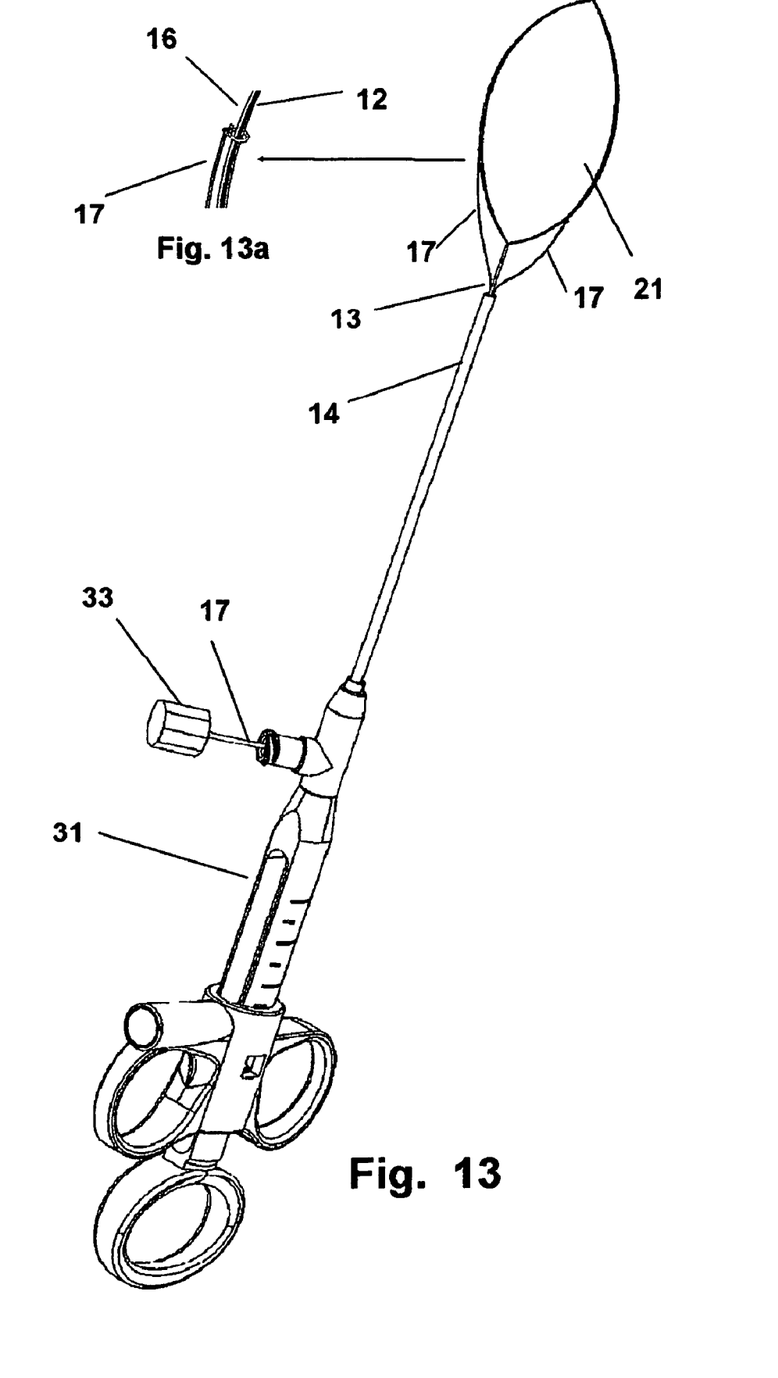
FIG. 13 shows another preferred mode of the device wherein a secondary control wire is provided engaged at a distal end to a plurality of means for restraint such as clips or ties which maintain the radially deployable members in a collapsed position during cauterization of tissue.
FIG. 13a shows a closeup view of the release wire engagement to the restraint device of FIG. 13.
Figures 14, 14A:
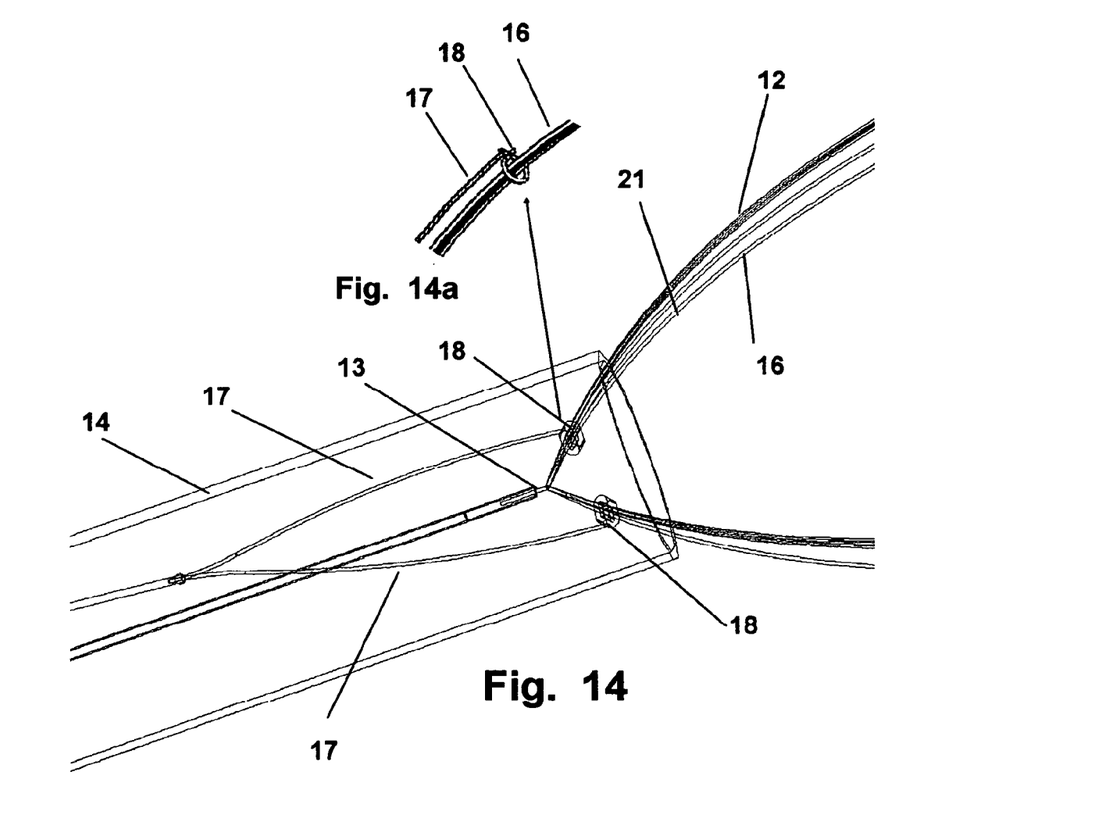
FIG. 14 shows radially deployed members in their collapsed position held by the restraints shown as ties prior to retraction of the control wire to release the deployable members to form a capture component.
FIG. 14a shows a closeup view of the release wire engagement to the restraint device of FIG. 14.

Another especially preferred mode of the device 10 is shown in FIGS. 13-14. This mode of the device 10 provides the surgeon with an especially useful surgical component in that it will allow for the cutting and cauterizing of one or a plurality of pieces of tissue prior to the release of the restraints to initiate the deployment of the members 16 to form a capture component 21 to thereafter allow for capture and removal the tissue 19 as in FIG. 12.

As shown in FIGS. 13-14 the device 10 in an especially preferred mode, employs a control wire 13 for translation of the loop 12 and deployable members 16 and also a separate release wire 17 which is engaged at a pair of distal ends, to a plurality of restraints 18 which are shown as ties such as in FIG. 13b. However, any means for restraint which may be selectively released by retracting the release wire 17 as would occur to those skilled in the art is anticipated within the scope of this invention.

As noted, in this mode of the device 10 the members 16 are maintained in their collapsed position with the loop 12 by the restraints 18 until the surgeon fully extends the members 16 and loop 12 from the insulating catheter 14 with the control wire 13 and subsequently retracts the release wire 17 to release the restraints 18. Control of the release wire 17 is shown accessible under cap 33 however other means to control the release wire as would occur to those skilled in the art is anticipated.

This mode of the device 10 is structured to yield an especially useful function during a surgery. On many occasions during surgery, the surgeon will need to remove and cauterize tissue 19 (FIG. 12) at a plurality of locations inside the body of the patient. Since the loop 12 attached to the members 16 in their collapsed position, heats the tissue for cutting and cauterizing when placed in to contact with the tissue and the loop 12 energized with electrical current to the grounded patient, it is important to maintain the members 16 in their retracted position for the duration of cutting and cauterizing. This mode of the device 10 provides that function by maintaining the restraints 18, insulated within the lumen or catheter 14 or other instrument during the ongoing cauterization process wherein the loop 12 is placed in contact with tissue and then energized with electrical current to create heat at the site of the tissue and grounded patient.

Maintaining the restraints 18 in a first position shown in FIG. 14, insulated within the channel of the catheter 14, thereby provides a means to protect the restraints 18 from melting or releasing due to heat generated in the loop 12 or members 16 adjacent to the restraints. Since the covered restraints 18 are maintained out of contact with tissue for the duration of the cutting and cauterization by the surgeon, until they are translated from the distal end of the catheter 14, there is no chance they may melt from being energized by tissue contact, or that the restraint 18 will melt due to the loop 12 or members 16 become heated in the area of the restraints 18. So maintained inside the catheter 14, the restraints 18 will maintain the members 16 in a collapsed position against the loop 12 for the duration of cutting and cauterization of tissue.

The surgeon can thus deploy the forward portion of the capture component 21 in the collapsed state formed by the members 16 and loop 12, from the distal end of the passage of the catheter 14. Once so deployed, the surgeon can energize the loop 12 to cut and cauterized the patient at a plurality of positions as needed for the procedure. All the while, the restraints 18 are safely maintained inside the catheter 14. This allows the surgeon to maintain the device 10 positioned continually inside the patient for the duration of the procedure without a release of the restraints 18 which might require removal and insertion of a new capture component 21 every time the restraints 18 become released should the surgeon wish to cauterize again.

A handle assembly 31 shown in FIG. 13 in a conventional fashion would have a control knob 33 wherein the control knob 33 would be removed to access and operate the release wire 17. Upon completion of the cutting and cauterizing of tissue at one or a plurality of different positions, once the members 16 and loop 12 have been translated fully from the distal end of the catheter 14, the control knob 33 would be released to allow manipulation of the control wire 17 to release the restraints 18 to thereby allow the members 16 to radially deploy to form the capture component 21. While depicted as an oval loop, the device 10 in this and all modes as noted may be formed in any shape or configuration in which the members 16 may be shaped and which will adapt the ultimate formed capture component 21 to the task at hand.

The method and components shown in the drawings and described in detail herein disclose arrangements of elements of particular construction, and configuration for illustrating preferred embodiments of structure of the present surgical device. It is to be understood, however, that elements of different construction and configuration, and using different steps and process procedures, and other arrangements thereof, other than those illustrated and described, may be employed for providing a surgical retrieval device and method in accordance with the spirit of this invention.

As such, while the present invention has been described herein with reference to particular embodiments thereof, a latitude of modifications, various changes and substitutions are intended in the foregoing disclosure, and will be appreciated that in some instance some features of the invention could be employed without a corresponding use of other features, without departing from the scope of the invention as set forth in the following claims. All such changes, alternations and modifications as would occur to those skilled in the art are considered to be within the scope of this invention as broadly defined in the appended claims.

Further, the purpose of the foregoing abstract of the invention, is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting, as to the scope of the invention in any way.

What is claimed is:

1. A surgical apparatus for deployment from a distal end of a catheter, comprising:
    a loop, said loop having a first end, said first end opposite a second end which is operatively engaged with a control wire and configured for translation through a lumen of said catheter between an insertion end and said distal end;
    a plurality of radially positionable shaped members having first ends and second ends, said first ends in operative engagement, to one of said loop or said control wire, said shaped members formed of insulated or non conductive material;
    each respective said shaped member having a deployed position around a center axis, and having a collapsed position in a stacked configuration against a side surface of said loop;
    said loop and said members in said deployed position forming a basket-like capture component;
    means to bias said members to said deployed position;
    means to restrain said shaped members in said collapsed position;
    said loop and shaped members translationally positionable by a translation of said control wire, to a first position with a first portion of said loop adjacent to said first end thereof, deployed from said lumen and with a remainder of said loop, and said means to restrain said shaped members maintained within said lumen;
    said loop and shaped members positionable by a said translation of said control wire, to a second position, with said loop and said shaped members still in said collapsed position, fully deployed from said lumen at said distal end of said catheter,
    means for release of said shaped members from said collapsed position;
    said loop uninsulated and energizable for cauterization on contact with tissue, in either of said first portion or said second position at a plurality of locations with said shaped members concurrently in said collapsed position thereby providing a maximized view of each said cauterization; and
    said shaped members translated to said second position, releasable from said collapsed position with said means for release of said shaped members from said collapsed position to move to said deployed position to form said capture component.

2. The surgical apparatus of claim 1 wherein said means for release of said shaped members from said collapsed position comprises:
    a release wire, said release wire having a control portion at a first end and a pair of distal ends in communication with a pair of restraints providing said means to restrain said shaped members in said collapsed position and holding said shaped members stacked against said loop; and
    said distal ends of said release wire retractable by a translation of said release wire toward said insertion end of said catheter, to cause a release of said restraints.

3. The surgical apparatus of claim 2 wherein said loop forms a mouth of said capture component when said members are in said deployed position.

4. The surgical apparatus of claim 3 wherein:
    each said restraint employed for means to restrain said shaped members in said collapsed position is a flexible member encircling said shaped members.

5. The surgical apparatus of claim 2 wherein:
    each said restraint employed for means to restrain said shaped members in said collapsed position is a flexible member encircling said shaped members.

6. The surgical apparatus of claim 1 wherein said loop forms a mouth of said capture component when said members are in said deployed position.

7. The surgical apparatus of claim 3 wherein:
    said means to restrain said shaped members in said collapsed position is a flexible member encircling said shaped members.

8. The surgical apparatus of claim 1 wherein:
    said means to restrain said shaped members in said collapsed position is a flexible member encircling said shaped members.

* * * * *